Sept. 16, 1947. M. S. WHITE Re. 22,916

METHOD AND APPARATUS FOR CONDUCTING ELECTROCARDIOGRAPHIC EXAMINATIONS

Original Filed May 22, 1942 4 Sheets-Sheet 1

INVENTOR
MAJOR S. WHITE
BY Francis P. Sandermann and Joseph H. Crowe
ATTORNEYS

METHOD AND APPARATUS FOR CONDUCTING ELECTROCARDIOGRAPHIC EXAMINATIONS
Original Filed May 22, 1942 4 Sheets-Sheet 2
Fig. 2.
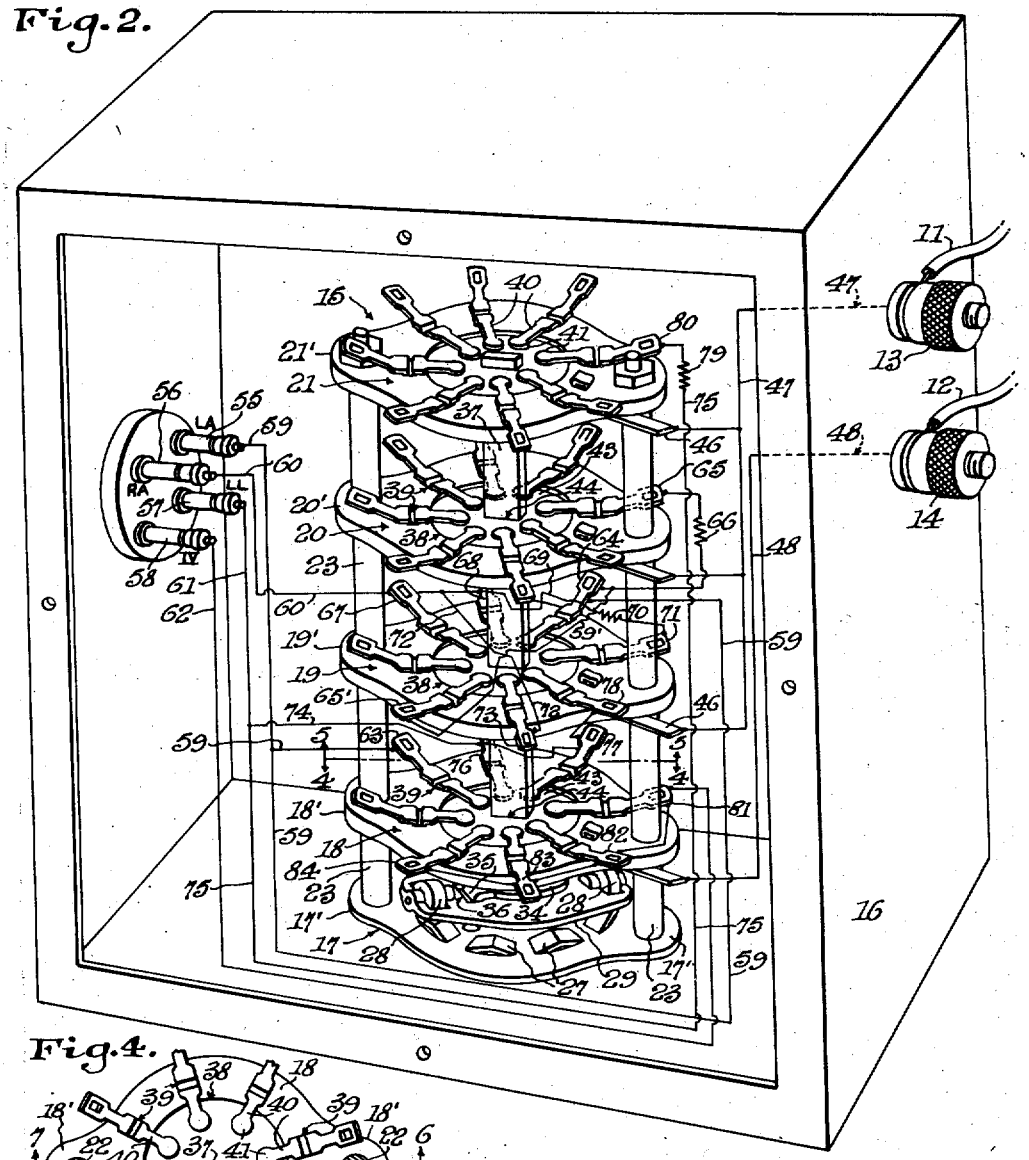
Fig. 4.
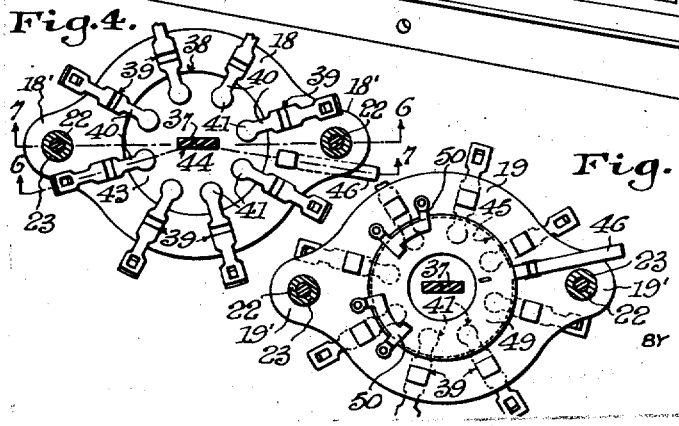
Fig. 5.
INVENTOR
MAJOR S. WHITE
BY Francis J. Sandusky and Joseph H. Brown
ATTORNEYS METHOD AND APPARATUS FOR CONDUCTING ELECTROCARDIOGRAPHIC EXAMINATIONS
Original Filed May 22, 1942 4 Sheets-Sheet 3
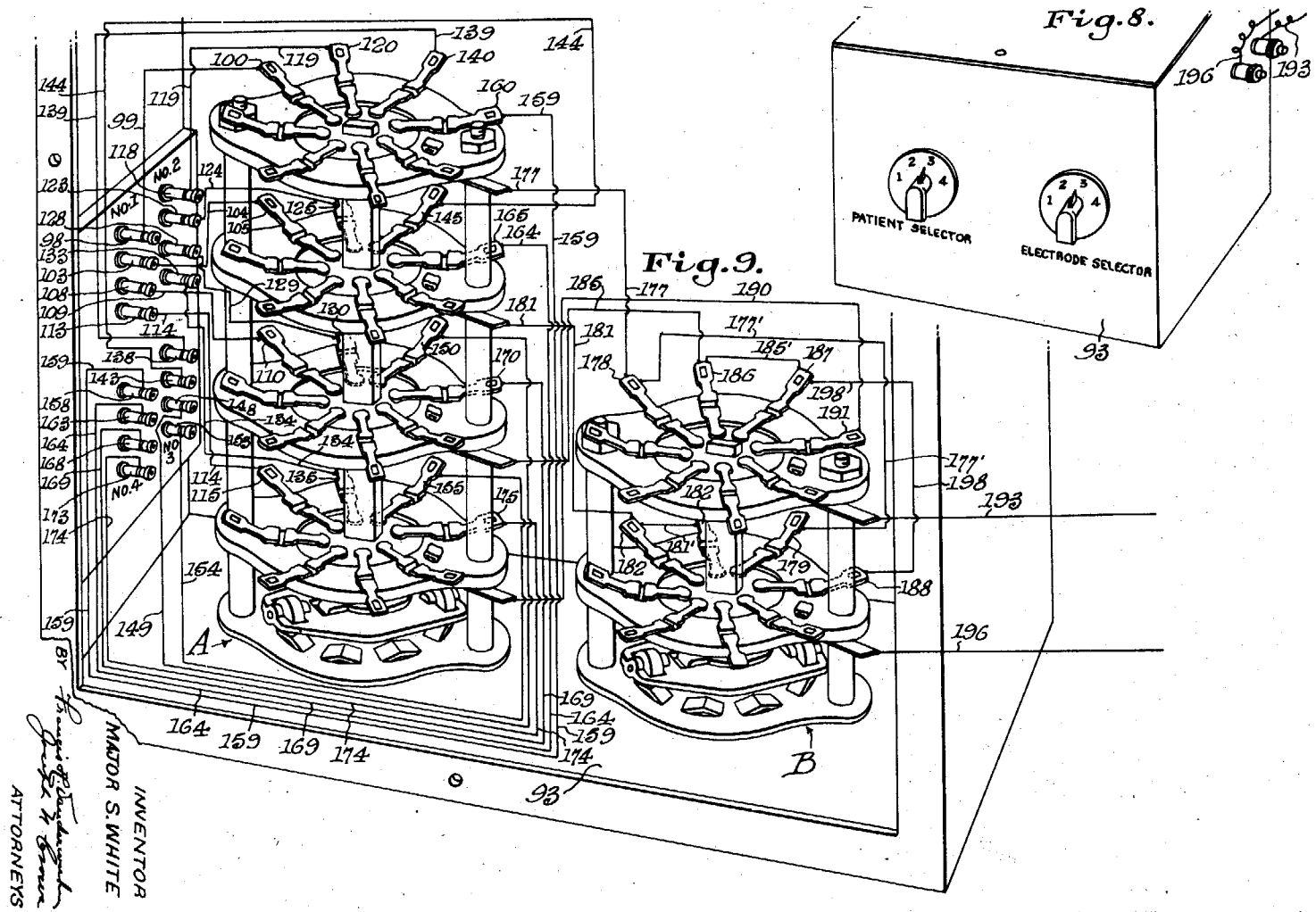
INVENTOR
MAJOR S. WHITE
BY Francis P. Vandervoort
Joseph H. Crowe
ATTORNEYS

METHOD AND APPARATUS FOR CONDUCTING ELECTROCARDIOGRAPHIC EXAMINATIONS

Original Filed May 22, 1942 4 Sheets-Sheet 4

INVENTOR
MAJOR S. WHITE
BY Francis P. Sandmyer and Joseph H. Brown
ATTORNEYS

Reissued Sept. 16, 1947

Re. 22,916

UNITED STATES PATENT OFFICE 22,916

METHOD AND APPARATUS FOR CONDUCTING ELECTROCARDIOGRAPHIC EXAMINATIONS

Major Samuel White, Arlington, Va.

Original No. 2,400,583, dated May 21, 1946, Serial No. 444,080, May 22, 1942. Application for reissue April 18, 1947, Serial No. 742,403.

12 Claims. (Cl. 128—2.06)

(Original granted under the act of March 3, 1883, as amended April 30, 1928; 370 O. G. 757)

The invention described herein may be manufactured and used by or for the Government for governmental purposes, without the payment to me of any royalty thereon.

This invention relates generally to electrocardiographs but more particularly to a method and means for controlling the path of current through electrodes contacting various parts of the body or bodies of one or more patients under examination to determine heart voltages with respect to different current paths.

Heretofore in making heart examinations it has been common practice to attach one electrode to each of the three limbs of the body of a person during examination and to selectively determine the voltages existing between these points. It has been found desirable in the diagnosis for certain diseases to provide an additional electrical reference point with respect to which the potential at other points and through various paths (including the arms and legs) may be determined. It has been known heretofore from clinical experiments that one such desirable reference point may be obtained by simultaneously placing electrodes on three limbs of the patient and connecting each of these electrodes through a high resistance to a common point. Using this common point as an electrical reference point, the voltage between this point and any other points on the body may be readily determined.

In the prior devices electrical switch means have been provided for pairing the electrodes from the different limbs for determining the potential difference existing therebetween but with these prior devices it is impossible to obtain the reference point, known as the Wilson potential, and to determine the voltage between this point and the other points on the body without removing the connecting wires to the different electrodes.

In the past when it was desired to obtain the potential over the precordium it was necessary to remove one of the limb electrodes and use it as an exploratory electrode in combination with any other reference point on the body. This destroyed the possibility of obtaining the Wilson zero point, or other reference points without requiring considerable time and inconvenience in changing the electrodes or connections to the electrodes.

In accordance with the present invention, means are provided for fixing and keeping an electrode in contact with each of three of the limbs of a person throughout the period of treatment, providing an electrical connection to each of said electrodes to establish an electrical reference point corresponding to each electrode and selectively connecting each of these electrodes in such a manner as to provide a fifth electrical reference point and means for measuring the potential difference between all of the combinations of pairs of these electrical reference points without disturbing the limb electrodes. This is a very important feature since it facilitates the obtaining of several combinations of readings in a minimum of time before the conditions under which the tests are being made have changed. For instance, when making such heart examinations it is well known that examinations are taken when the person is first in the rested and relaxed condition and then after the patient has been instructed to perform certain physical exercises in order to stimulate the action of the heart, or vice versa. It is essential that all of the tests be completed before the rate of the action of the heart has appreciably diminished. By the use of the present invention investigations of the heart under these conditions is greatly facilitated.

One object of the invention is to provide a device, used in conjunction with an electrocardiograph by which various current paths from the patient to the electrocardiograph may be selected without the necessity of changing the location of the electrodes on the body of the patient to thus facilitate speed and ease of examination.

Another object of the invention is to provide for use, with the electrocardiograph, of precordial electrodes in addition to the electrodes now commonly used, and to adapt the instrument for the instantaneous selection of current paths from any of the electrodes connected to one or more patients.

With these and other objects in view, the invention consists in a novel method of cardiographic examination of patients, and novel details of construction, combination and arrangement of parts of the apparatus devised to effect the examination, as will be more fully hereinafter set forth and pointed out in the claims.

Referring to the figures in which like parts are indicated by similar reference characters:

Fig. 2 is a perspective view of the housing shown in Fig. 1, with top removed, showing the interior thereof with circuit control mechanism and lead connectors;

Fig. 4 is a horizontal section taken on the line 4—4 of Fig. 2, looking in the direction of the arrows;

Fig. 5 is a horizontal section taken on the line 5—5 of Fig. 2, looking in the direction of the arrows;

Fig. 8 is a perspective view of a modified form of the device showing the exterior of the housing enclosing the circuit control apparatus adapted to form circuits to an electrocardiograph through various pairs of electrodes connected to a group of patients;

Fig. 9 is a perspective view of the housing shown in Fig. 8 with the top removed showing the interior thereof with circuit control mechanism and lead connectors;

Of the instruments described herein, that shown in Figs. 1 to 7 inclusive is adapted to be used with a single patient and was devised to obtain precordial leads by the various recommended methods as well as the standard leads, so as to obviate the changing of lead wires or electrodes during the process.

Figure 10:
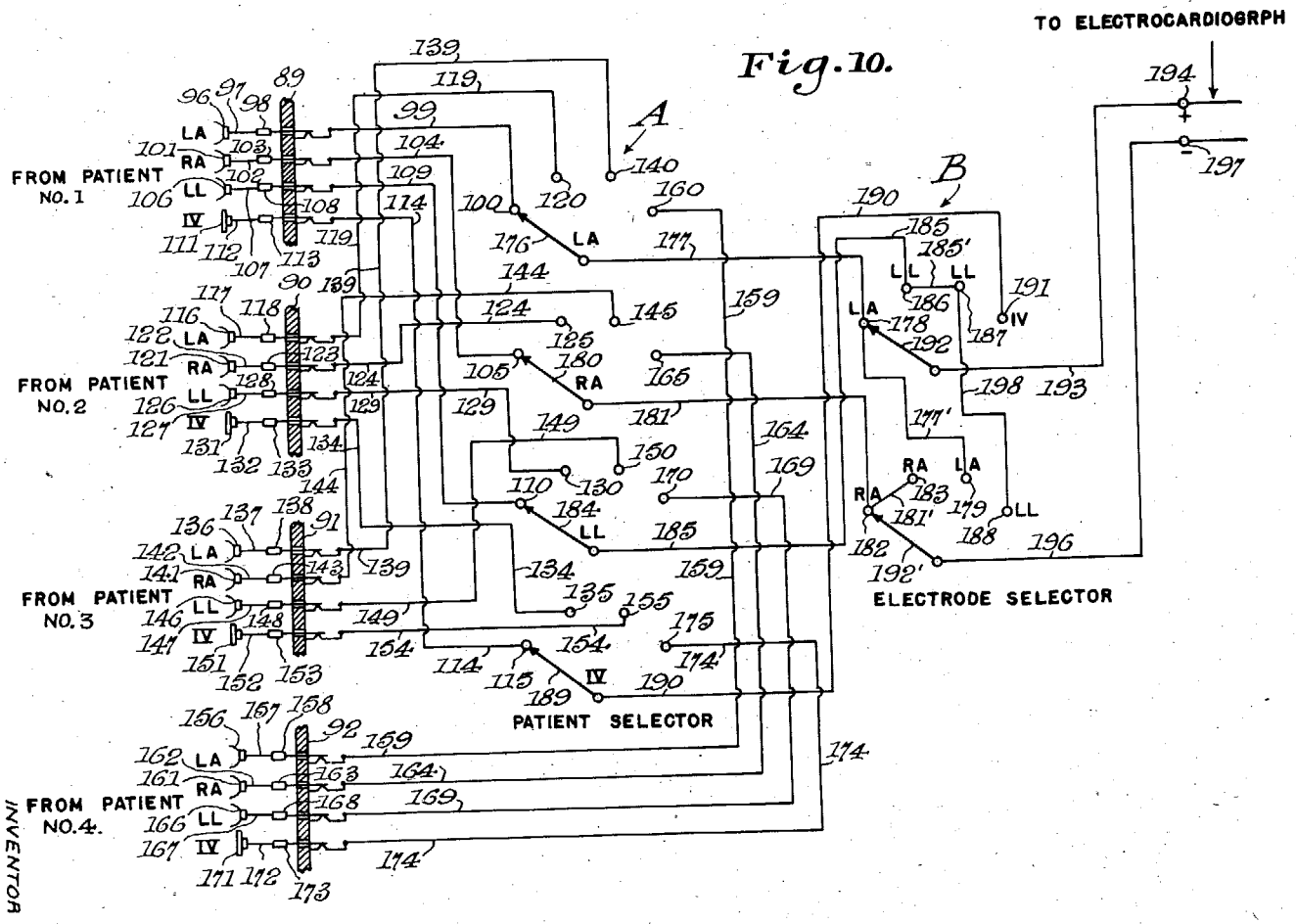
Fig. 10 is a diagrammatic view of the multiple patient circuit control mechanism.

The modified form of instrument shown in Figs. 8 to 10 inclusive was designed so that, by operating a switch, it would be possible to connect several patients in succession to a single electrocardiograph machine at a rapid rate, as may be required in certain investigations, or in the examination of large groups.

Figure 3:
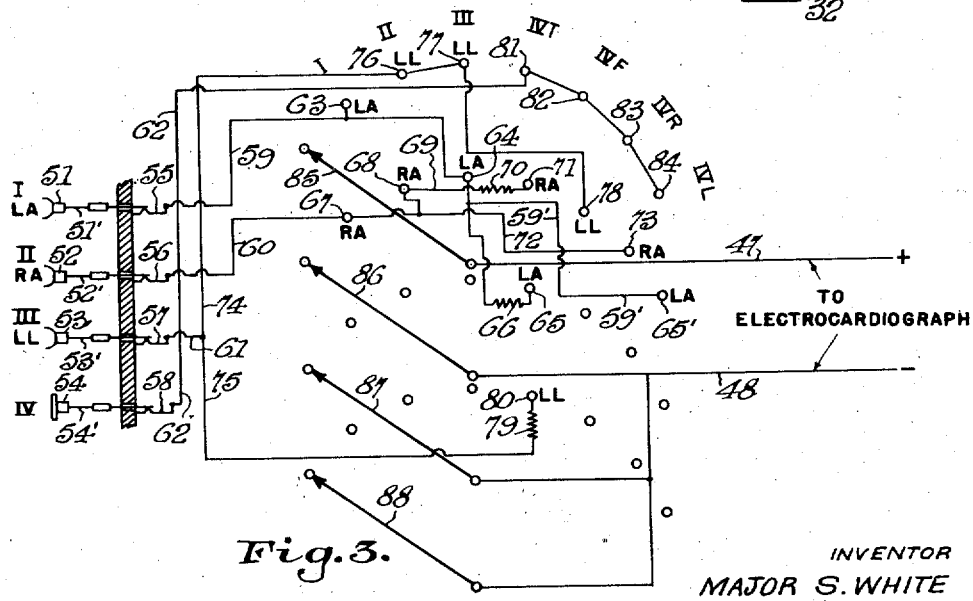
Fig. 3 is a diagrammatic view of the circuit control mechanism shown in Figs. 1 and 2.

Referring to the single patient instrument, the wiring diagram Fig. 3 shows the arrangement for obtaining the three standard leads, I, II, III and lead IV of the precordial or exploring electrode. By the simple additional connections as shown diagrammatically in Fig. 3, the device can be arranged so that one-step movements of the switch will successively pair, electrically, the precordial or exploratory lead (through means of the various switch contacts) with the leads which are connected respectively to the left arm, right arm and the left leg. The different switch positions connect the different electrodes fixed to the body, as well as the exploratory electrode which is adapted to be placed at different points on the body during examination, so that the values of the current and voltage developed in the body due to heart action may be determined by an electrocardiograph between the following points: position I, left arm and right arm; position II, left leg and right arm; position III, left leg and left arm; and position IVT, the exploratory electrode which may be placed at any point on the body, including the precordium or chest and the so-called "zero potential of Wilson."

The operation of an electrocardiograph is based upon the fact that the action of the heart in the human body is accompanied by small voltage impulses of the order of .001 volt between the arms or legs. When taking electrocardiograph readings between any two points on the human body there are simultaneously present a plurality of electrical currents or potentials of different polarities and values. However, there is usually a resultant predominating electrical current and potential which gives an indication of the heart axis. In order to reduce as far as possible the effect of the disturbing potentials it has been found that a valuable electrical reference point may be obtained by connecting each of the arms and one of the legs, usually the left, through suitable non-inductive resistances to a common point. By this arrangement the resultant electrical current and potentials are substantially zero at this point. This is commonly referred to in the medical profession as the "zero potential of Wilson" although, of course, it will be readily understood that this is merely an electrical reference point and is obtained by connecting leads or conductors from the left and right arms and the left leg of the patient each through a 5,000 ohm non-inductive resistance. At this central point or terminal, the potential is so near zero throughout the heart cycle that it may be so considered without encountering serious error. When the switch is moved to position IVT, as shown in Figure 3, the exploratory electrode is electrically paired with this central terminal electrical reference point, or "zero potential of Wilson"; at position IVF with the electrode on the left leg; at position IVR with the electrode on the right arm; and at position IVL with the electrode on the left arm. It will be readily understood that when the switch is in such a position that arm 85 (Figure 3) connects one of the terminals of the electrocardiograph to the exploratory electrode (positions IVT, IVF, IVR and IVL) the exploratory electrode may be placed at any point on the body including the precordium or chest position so that the potential at any point on the body may be measured, selectively, with respect to the points on the body in contact with the electrodes on the left arm, right arm, left leg and the so-called "zero potential of Wilson." By referring to Figure 3 it will be seen that when the arm of the switch 85 rests on the contact 81 the switch arm 86 will rest on contact 71, the switch arm 87 will rest on contact 65 and the switch arm 88 will rest on contact 89 thereby establishing the electrically neutral reference point herein referred to as the "zero potential of Wilson" and will connect this neutral electrical reference point to the conductor 48 which is adapted to be connected to one terminal of the electrocardiograph. As shown, switch arm 85 is connected to conductor 47 which is adapted to be connected to the other terminal of the electrocardiograph.

The term "leads" appearing herein is used in the sense to which it is normally referred in the medical profession to indicate the electrodes which are placed in contact with the different points on the body together with their associated electrical conductors. For a definition of the "zero potential of Wilson" reference is made to "Clinical aspects of the electrocardiogram," by Harold E. P. Pardee, M. D., fourth edition, revised, published by Paul B. Hoeber, Medical Book Dept., Harper & Bros. Inc., page 327.

The term "precordium or exploratory electrode" is used ordinarily in the medical profession to designate the "fourth" electrode described herein which is not adapted to be fixed during examination to a point on the body of the patient. It is sometimes referred to solely as the "precordial" lead because the precordium is one of the main points or positions on the body with respect to which it is desired to measure the electrical voltage on one of the limbs, although during examination it is usually moved to various points on the body and its use is not at all limited to the precordium position. It is believed that the term "exploratory" is a much more apt term which defines the use of this lead.

In the multiple patient instrument, four electrodes are attached to the patient; three to the usual extremities and one, a precordial or exploring electrode, to the precordium. Each electrode may be connected to a four-prong polarized plug by a four conductor cable or to regular plug-in connectors as shown in Fig. 10. Any number of patients (in this case four) may be so connected. Each plug is inserted into a polarized plug-in connector or jack on the left-hand side of the switch box. This switch box has two control switches. The first (A) (Figs. 9 and 10) selects the patient whose record is to be taken at the moment. The second switch (B) (Figs. 9 and 10) selects any one of the four leads which it is desired to record from the electrodes connected to a patient. On the right hand end of the switch box is a polarized jack or plug-in connection in which is inserted a plug connected to two wires leading directly to the electrocardiograph. Any two lead wires of the electrocardiograph may be connected to the plug with due regard to polarity. The corresponding lead is then selected by the lead switch on the control panel of the electrocardiograph.

With the switches used in the instrument, there are a sufficient number of contact points so as to make it possible to add more patients if so desired, or additional combinations of leads.

Figure 1:
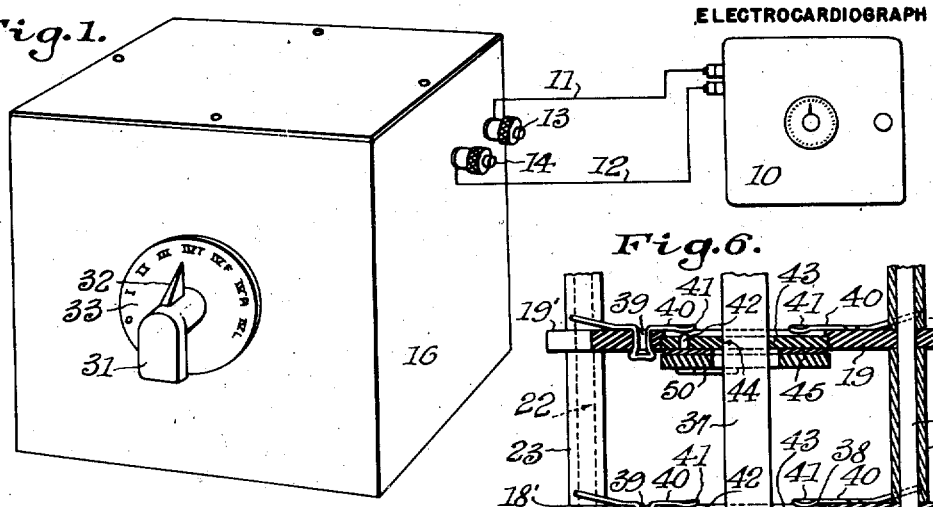
Fig. 1 is a perspective exterior view of the housing enclosing the circuit control device for a single patient showing the selector dial and leads to an electrocardiograph.
Figure 6:
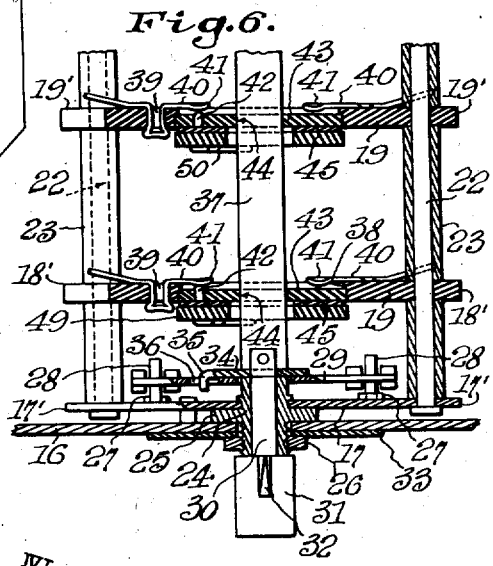
Fig. 6 is a vertical section taken on the line 6—6 of Fig. 4.
Figure 7:
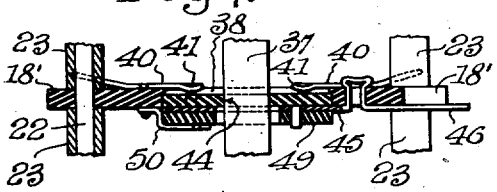
Fig. 7 is a detail vertical section taken on the line 7—7 of Fig. 4.

Referring to Fig. 1, the numeral 10 indicates an electrocardiograph provided with leads 11 and 12 which are connected to the terminals 13 and 14 of a selector 15 shown in Figs. 2, 6 and 7.

The selector 15 which is mounted within a housing 16 is of the rotary type and is constructed with a disc shaped index base 17 having laterally projecting ears 17', and a plurality of switch bases or plates 18, 19, 20 and 21 formed of insulating material and provided with laterally projecting ears 18', 19', 20' and 21' drilled to receive bolts 22.

The index base 17 and the switch bases 18, 19, 20 and 21 mounted upon the bolts 22 are spaced from each other by sleeves 23.

The index base is provided centrally with a collar 24 having a flange 25 adapted to form a seat and a threaded portion which is adapted to be fitted into an opening in the front wall of the housing 16 and retained therein by means of a nut 26. The index base 17 is provided with circumferentially spaced raised portions 27 over which rollers 28, attached to the opposite sides of an index arm 29, pass, as will be further described.

Within the sleeve member 24 which is attached to the index plate 17 is rotatably mounted an indicator shaft 30 to which is rigidly connected a turning knob 31 provided with a pointer 32 which is adapted to move over a dial 33 attached to the housing 16. The end of the shaft 30 is squared to fit a central opening in a turning disc 34.

The turning disc 34 is provided with a curved projection 35 which fits into an opening 36 in the index arm 29 so that with rotation of the indicator shaft 30 the index arm which is formed of spring metal is revolved so that the rollers pass over the raised portions of the index plate to indicate a number of contact points marked on the dial 33. The indicator shaft 30 is slotted to provide for the attachment of a non-circular shaft 37 which projects through centrally located circular openings 38 in the switch bases.

In addition to the large central opening 38, the switch bases 18, 19, 20 and 21 are each provided with a circumferentially arranged row of rectangular openings 39. Within these rectangular openings 39 are fitted a plurality of spring fingers or contact members which are generally designated by the reference character 40. These fingers are crimped so that a portion of them may, due to their elasticity, clamp themselves within the openings, as shown in Fig. 6. In the discussion relative to the operation of the device hereinafter to be given, the fingers 40 will each be given individual reference characters. These spring fingers are each provided with semi-spherically formed ends 41 which are adapted to electrically contact bridging members 42 which are inserted within openings in rotatable discs 43 mounted on the central non-circular shaft 37.

The rotatable discs 43 are circular, formed of insulating material, and provided with a central slotted opening 44 adapted to fit the non-circular shaft 37. Beneath each of these discs 43, and contacting them, is placed a metallic non-rotatable disc 45, which discs are each provided with a radially extending projection 46 connected to a lead wire 47 or 48.

These metallic discs 45 are rigidly attached to a lower insulating disc 49 which is supported by brackets 50 which extend from the switch bases and are provided with curved projections which enter openings in the discs 49.

As shown in Fig. 7 the metallic discs 49 are retained in position by the brackets 50, and projections 40 which are crimped in the same manner as the fingers 40 so that the crimped portions may be inserted into an opening in the switch bases 18, 19, 20 and 21.

The electrodes 51, 52, 53 and 54 shown diametrically in Fig. 3, and which are attached to the left arm, right arm, left leg and to a precordial electrode on a patient, are connected to the patient leads 51', 52', 53' and 54' which are in turn connected to the plug-in connectors 55, 56, 57 and 58. From these connectors, selector leads 59, 60, 61 and 62 pass to spring fingers or contacts generally termed 40 on the switch bases.

The connector 55 is connected through the conductor 59 to the contact 63 on switch plate 18, contact 64 on switch plate 19, and to the contact 65 on switch plate 20 through the resistance 66, and through a branch lead 59' to contact 65 on switch plate 19.

The connector 56 is connected through the conductor 60 to the contacts 67 and 68 on switch plate 19 and through the branch lead 69 and resistance 70 to contact 71 on switch plate 19, and through branch lead 72 to contact 73 on switch plate 19.

The connector 57 is connected through the conductor 61 to branch leads 74 and 75. The branch lead 74 is connected to contacts 76 and 77 on switch plate 18 and to contact 78 on switch plate 19. The branch lead 75 is connected through resistance 79 to contact 80 on switch plate 21.

The connector 58 is connected through conductor 62 to the contacts 81, 82, 83 and 84 on switch plate 18.

The movable contacts which are mounted in the centrally located insulating discs 43 as shown in Figs. 4 and 6 are adapted to rotate with the non-circular shaft 37 and are indicated by the numerals 85, 86, 87 and 88 in the diagrammatic representation in Fig. 3. In this figure the switch blades 85, 86, 87 and 88 represent the metallic discs 45 and contacts 42 which are connected to the leads 47 and 48 as shown in Fig. 2.

It will be noted that any of patient circuits, i. e., from the left arm and right arm electrodes, are completed in the following manner: from the left arm through conductors to a spring arm 40 on a switch plate, and from the spring arm to a contact pin 42, and through a metallic disc 45 to the electrocardiograph, and from the electrocardiograph through a disc 45, through a pin 42 to another spring arm 40, and through a return lead to the electrode on the right arm of the patient.

In the multiple patient selector illustrated by Figs. 8, 9 and 10 the construction and arrangement of the plate members is similar to the single patient device.

In this device, two selectors are used both of which are attached to the front wall of a housing as illustrated in Figs. 8 and 9. Since the construction and operation of these selectors are the same as described above, it will only be necessary to describe their manner of selecting circuits by reference to the diagrammatic illustration as represented in Fig. 10.

In Fig. 10 the numerals 89, 90, 91 and 92 indicate portions of the side wall of the selector housing 93 in which are mounted four groups of plug connector elements for the reception of plug terminals at the extremities of the patient leads.

In order to trace the circuits connecting pairs of electrodes contacting the patients numbered 1, 2, 3 and 4, inclusive, the electrical connection from the left arm, right arm, left leg and the precordial electrode on each patient will be taken in the numerical order of the patients and traced first to the patient selector.

From patient No. 1: the left arm electrode 96 is connected by the patient lead 97 to the plug connector 98, and the plug connector 98 is connected through conductor 99 to the contact member 100 of the left arm group of the patient selector, indicated by the letters L. A.; the right arm electrode 101 is connected by lead 102 to connector 103, and the connector 103 is connected through conductor 104 to the contact member 105 of the right arm group of the patient selector, indicated by the letters R. A.; the left leg electrode 106 is connected by lead 107 to connector 108, and the connector 108 is connected through conductor 109 to the contact member 110 of the left leg group indicated by the letters L. L.; the precordial electrode 111 is connected by lead 112 to connector 113, and the connector 113 is connected through conductor 114 to contact member 115 of the precordial group of the patient selector, indicated by the numeral IV.

From patient No. 2: the left arm electrode 116 is connected by the patient lead 117 to the plug connector 118, and the plug connector 118 is connected through conductor 119 to the contact member 120 of the left arm group of the patient selector, indicated by the letters L. A.; the right arm electrode 121 is connected by lead 122 to connector 123, and the connector 123 is connected through conductor 124 to the contact member 125 of the right arm group of the patient selector, indicated by the letters R. A.; the left leg electrode 126 is connected by lead 127 to connector 128, and the connector 128 is connected through conductor 129 to the contact member 130 of the left leg group indicated by the letters L. L.; the precordial electrode 131 is connected by lead 132 to connector 133, and the connector 133 is connected through conductor 134 to contact member 135 of the precordial group of the patient selector, indicated by the numeral IV.

From patient No. 3: the left arm electrode 136 is connected by the patient lead 137 to the plug connector 138 and the plug connector 138 is connected through conductor 139 to the contact member 140 of the left arm group of the patient selector, indicated by the letters L. A.; the right arm electrode 141 is connected by lead 142 to connector 143 and the connector 143 is connected through conductor 144 to the contact member 145 of the right arm group of the patient selector, indicated by the letters R. A.; the left leg electrode 146 is connected by lead 147 to connector 148, and the connector 148 is connected through conductor 149 to the contact member 150 of the left leg group indicated by the letters L. L.; the precordial electrode 151 is connected by lead 152 to connector 153, and the connector 153 is connected through conductor 154 to contact member 155 of the precordial group of the patient selector indicated by the numeral IV.

From patient No. 4: the left arm electrode 156 is connected by the patient lead 157 to the plug connector 158, and the plug connector 158 is connected through conductor 159 to the contact member 160 of the left arm group of the patient selector, indicated by the letters L. A.; the right arm electrode 161 is connected by lead 162 to connector 163, and the connector 163 is connected through conductor 164 to the contact member 165 of the right arm group of the patient selector, indicated by the letters R. A.; the left leg electrode 166 is connected by lead 167 to connector 168, and the connector 168 is connected through conductor 169 to the contact member 170 of the left leg group indicated by the letters L. L.; the precordial electrode 171 is connected by lead 172 to connector 173, and the connector 173 is connected through conductor 174 to contact member 175 of the precordial group of the patient selector, indicated by the numeral IV.

The contact members of the left arm, right arm, left leg, and the precordial groups of the patient selector, are connected electrically to the contacts of the electrode group as follows: contact members 100, 120, 140 and 160 of the left arm group L. A. may be connected selectively, through the rotatable contact member 176 and leads 177 and 177′, to the contacts 178 and 179 of the electrode selector; contact members 105, 125, 145 and 165 of the right arm group R. A. may be connected selectively through the rotatable contact member 180 and leads 181 and 181′ to the contacts 182 and 183 of the electrode selector; contact members 110, 130, 150 and 170 of the left leg group L. L.—may be connected selectively through the rotatable contact member 184 and leads 185, 185′, and 186 to contacts 186, 187 and 188 of the electrode selector; and contact members 115, 135, 155, and 175 of the precordial electrode group IV may be connected selectively through the rotatable contact member 189 and the lead 190 to contact 191 of the electrode selector.

Contacts 178, 186, 187 and 191 of the electrode selector may be connected selectively through the rotatable contact member 192 and leads 193 to the positive terminal 194 of the electrocardiograph, and contacts 182, 183, 179 and 188 may be connected through the rotatable contact member 192′ and lead 196 to the negative terminal 197 of the electrocardiograph.

To illustrate the operation of both the single patient and multiple patient apparatus, a circuit through a pair of electrodes to the electrocardiograph in each device will be described and with this description and the description of the entire wiring system as given above, it will be a simple matter to trace any of the circuits used.

If a circuit through position I of the single patient device is chosen, then from the left arm electrode 51 (Fig. 3) the current will pass through lead 51', plug-in connector 55, conductor 59 to contact 63, and from contact 63 through switch blade 85 (which represents the metallic disc 45 in Fig. 6) to lead 47 of the electrocardiograph, and from lead 48 of the electrocardiograph through switch blade 86 to contact 67 and thence through conductor 60 to plug-in connector 56 to patient lead 52', and to the right arm electrode 52.

When the pointer is moved to position II, the circuit is from the left leg electrode 53 to terminal contact 76 through switch blade 85, through conductor 47 to the electrocardiograph and from the electrocardiograph through conductor 48 to switch blade 86, contact 68, to the right arm electrode 52.

For the third position, or when the pointer is moved to III on the dial, the circuit is from left leg electrode to terminal 77 through switch blade 85 through conductor 47 to the electrocardiograph and from the electrocardiograph through conductor 48 to switch blade 86, contact 64 to the left arm electrode 51.

At position IVT the circuit is from the precordial electrode 54 to contact 81 through switch blade 85 and conductor 47 to the electrocardiograph, and from the electrocardiograph through conductor 48 and respectively through switch blades 86, 87 and 88, contacts 77, 65 and 80 and resistances 70, 66 and 79 to the right arm, left arm and left leg electrodes 52, 51 and 53.

When the pointer is moved to IVF the circuit is from the precordial electrode 54 to contact 82 through switch blade 85 and conductor 47 to electrocardiograph and from the electrocardiograph through conductor 48, switch blade 47, and contact 78 to the left leg electrode 53.

When the pointer is moved to IVR the circuit is from the precordial electrode 54 to contact 83, through switch blade 85 and conductor 47 to the electrocardiograph and from the electrocardiograph through conductor 48, to contact 73, and through the switch blade 88 to the right arm electrode 52.

The pointer when moved to IVL completes a circuit from the precordial electrode 54 to contact 84, through switch 85 and conductor 47 to the electrocardiograph, and from the electrocardiograph through conductor 48, switch blade 86 and contact 65', to the left arm electrode 51.

The multiple device as mentioned above is provided with two selectors, a patient selector, having four positions, one for the selection of each of four patients, and an electrode selector having four positions, one for each of four circuits, namely, I from the left arm and right arm electrodes, II from the left leg and right arm electrodes, III the left leg and left arm electrodes, and IV the precordial and left leg electrodes.

The circuits for the I, II, III and IV positions of patients No. 1, No. 2, No. 3 and No. 4 are as follows:

Patient No. 1, position I (left arm and right arm). From left arm electrode 96 to contact 100, switch blade 176, contact 178, switch blade 192, contact 194 to electrocardiograph. From electrocardiograph to contact 197, switch blade 192', contact 182, switch blade 18, and contact 105 to right arm electrode 101.

Patient No. 1, position II (left leg and right arm). From left leg electrode 106 to contact 110, switch blade 184, contact 186, switch blade 192, contact 194 to electrocardiograph. From electrocardiograph to contact 197, switch blade 192', contact 182, switch blade 180, contact 183, contact 105, and to right arm electrode 101.

Patient No. 1, position III (left leg and left arm). From left leg electrode 106 to contact 110, switch blade 184, contact 187, switch blade 192, contact 194 to electrocardiograph. From electrocardiograph to contact 197, switch blade 192', contact 179, switch blade 173, contact 100, to left arm electrode 96.

Patient No. 1, position IV (precordial electrode and left leg). From precordial electrode 111 to contact 115, switch blade 189, contact 191, switch blade 192, contact 194 to electrocardiograph. From electrocardiograph to contact 197, switch blade 192', contact 188, switch blade 184, contact 110 to left leg electrode 106.

Patient No. 2, position I (left arm and right arm). From left arm electrode 122 to contact 120, switch blade 176, contact 178, switch blade 192, contact 194 to electrocardiograph. From electrocardiograph to contact 197, switch blade 192', contact 182, switch blade 180, contact 125 to right arm electrode 121.

Patient No. 2, position II (left leg and right arm). From left leg electrode 126 to contact 130, switch blade 184, contact 186, switch blade 192, contact 194 to electrocardiograph. From electrocardiograph to contact 197, switch blade 192', contact 183, switch blade 180, contact 125 and right arm electrode 121.

Patient No. 2, position III (left leg and left arm). From left leg electrode 126 to contact 130, switch blade 187, switch blade 192, contact 194 to electrocardiograph. From the electrocardiograph to contact 197, switch blade 192', contact 179, switch blade 176, contact 120, to left arm electrode 116.

Patient No. 2, position IV (precordial electrode and left leg). From precordial electrode 131 to contact 135, switch arm 189, contact 191, switch blade 192, contact 194 to electrocardiograph. From electrocardiograph to contact 197, switch blade 192', contact 188, switch blade 184, contact 130 to left leg electrode 126.

Patient No. 3, position I (left arm and right arm). From left arm electrode 142 to contact 140, switch blade 176, contact 178, switch blade 192, contact 194 to electrocardiograph. From electrocardiograph to contact 197, switch blade 192', contact 182, switch blade 180, contact 145 to right arm electrode 141.

Patient No. 3, position II (left leg and right arm). From left leg electrode 146 to contact 150, switch blade 184, contact 186, switch blade 192, contact 194 to electrocardiograph. From electrocardiograph to contact 197, switch blade 192', contact 183, switch blade 180, contact 145 to right arm electrode 141.

Patient No. 3, position III (left leg and left arm). From left leg electrode 146 to contact 150, switch blade 184, contact 187, switch blade 192, contact 194 to electrocardiograph. From electrocardiograph to contact 197, switch blade 192', contact 179, switch blade 176, contact 140 to left arm electrode 136.

Patient No. 3, position IV (precordial electrode and left leg). From precordial electrode 151 to contact 155, switch blade 189, contact 191, switch blade 192, contact 194 to electrocardiograph. From electrocardiograph to contact 197, switch blade 192', contact 188, switch blade 184, contact 150 to left leg electrode 146.

Patient No. 4, position I (left arm and right arm). From left arm electrode 156, contact 160, switch blade 176, contact 178, switch blade 192, contact 194 to the electrocardiograph. From the electrocardiograph to contact 197, switch blade 192', contact 182, switch blade 180, contact 105 to right arm electrode 101.

Patient No. 4, position II (left leg and right arm). From the left leg electrode 166 to contact 170, switch blade 184, contact 186, switch blade 192, contact 194 to the electrocardiograph. From the electrocardiograph to contact 197, switch blade 192', contact 183, switch blade 180, contact 165 to electrode 161.

Patient No. 4, position III (left leg and left arm). From left leg electrode 166 to contact 170, switch blade 184, contact 187, switch blade 192, contact 194 to the electrocardiograph. From the electrocardiograph to contact 197, switch blade 192', contact 179, switch blade 176, contact 140 to left arm electrode 136.

Patient No. 4, position IV (precordial electrode and left leg). From the precordial electrode 171 to contact 175, switch blade 189, contact 191, switch blade 192, contact 194 to the electrocardiograph. From the electrocardiograph to contact 197, switch 192', contact 188, switch blade 184, contact 170 to left leg electrode 166.

Although in the foregoing certain elements have been described as best adapted to perform the functions allotted to them, nevertheless it is to be understood that certain changes may be resorted to without departing from the spirit and scope of the invention as disclosed in the appended claims.

Having described my invention, what I claim as new and desire to secure by Letters Patent is:

1. In combination with an electrocardiograph, a selecting device comprising a patient selector provided with contact members electrically connected with electrodes attached to a plurality of patients, and a contact selector adapted to selectively contact said contact members; and an electrode selector provided with contact members connected electrically with said contact selector, and an additional contact selector connected with the leads of an electrocardiograph and adapted to selectivity contact the contact members of said electrode selector, whereby electrodes attached to any of the patients may be selectively connected with the leads of the electrocardiograph.

2. In combination with electrocardiograph, a selecting device comprising a patient selector provided with circularly arranged contact members electrically connected with electrodes attached to a plurality of patients, and a rotatable contact selector adapted to contact said contact members; an electrode selector provided with circularly arranged contact members connected electrically with said contact selector, and a rotatable contact selector connected with the leads of an electrocardiograph adapted to contact the contact members of said electrode selector to selectively establish circuits through the electrodes and the leads of the electrocardiograph.

3. In combination with an electrocardiograph, selecting devices comprising, a patient selector including a plurality of stationary contact members electrically connected to patient electrodes, and movable contact members adapted to selectively contact any of said stationary contact members; and an electrode selector including a plurality of stationary contact members electrically connected to the stationary contact members and the movable contact members of said patient selector, said electrode selector being provided with movable contact members connected electrically with an electrocardiograph and adapted to selectively contact any of said stationary contact members of said patient selector.

4. In an apparatus of the class described for group examination of a series of patients, the combination with an electrocardiograph machine including its positive and negative electrodes; of electrode connector means, a plurality of patient electrodes attached in groups to said connector means, each electrode group including a precordial and a series of limb electrodes adapted to be operatively associated with one of said patients, the respective groups serving to connect simultaneously a series of patients with said connector means, a patient selector permanently connected with said connector means and operable for selecting one of said patients and the electrode group associated therewith, and switching means in electrical relation with the patient selector and with the positive and negative electrode terminals of said electrocardiograph machine for establishing electrocardiographic leads from the patient and electrode group selected by said patient selector, to said electrocardiograph machine.

5. In an apparatus of the class described for group examination of a series of patients, the combination with an electrocardiograph machine including its positive and negative electrodes; of electrode connector means, a plurality of patient electrodes attached in groups to said connector means, each electrode group including a precordial and a series of limb electrodes adapted to be operatively associated with one of said patients, the respective groups serving to connect simultaneously a series of patients with said connector means, a patient selector permanently connected with said connector means and operable for selecting one of said paients and the electrode group associated therewith, and switching means in electrical relation with the patient selector and with the positive and negative terminals of said electrocardiograph machine for connecting a pair of electrodes in the electrode group selected by said patient selector with said electrocardiograph machine.

6. In combination with an electrocardiograph having input terminals, a plurality of at least three electrodes adapted to be kept in contact with different points on the body of a person during examination, an additional electrode adapted to be placed at will in contact with different points of the body for exploratory purposes, and means electrically interposed between said input terminals and said electrodes selectively to pair, electrically any of said electrodes, and to connect said plurality of electrodes to a common point and to pair said additional electrode with said common point.

7. In combination with an electrocardiograph having input terminals, a plurality of electrodes some of which are adapted to be kept in contact with a plurality of spaced points on the body of a person during examination, at least one additional electrode adapted to be placed at will on the body of the person as an exploratory electrode, and means electrically interposed between said input terminals and said electrodes for alternatively, electrically associating any two of said plurality of electrodes into an electrical pair and for electrically, associating with said additional electrode any one of said plurality and a point electrically common to said plurality of electrodes.

8. In combination with an electrocardiograph having input terminals, a plurality of electrodes some of which are adapted to be kept in contact with a plurality of spaced points on the body of a person during examination, at least one additional electrode adapted to be placed temporarily in contact with different points on the body of the person as an exploratory electrode, means electrically interposed between said input terminals and said electrodes for selectively forming an electrical pair including one of said plurality of electrodes and said additional electrode and for electrically associating into an electrical pair two of said plurality of electrodes, and means including said first named means for electrically connecting said plurality of electrodes with an electrically common point and associating in an electrical pair said common point and said additional electrode.

9. In combination with an electrocardiograph having input terminals, a plurality of electrodes some of which are adapted to be detachably fixed to a plurality of spaced points on the body of a person during examination, at least one additional electrode adapted to be placed temporarily on the body of the patient as an exploratory electrode, non-inductive resistances connected between each of said electrodes and a common point, and means electrically interposed between said input terminals and said electrodes for selectively forming an electrical pair including said additional electrode and said point, and for electrically associating into an electrical pair any two of said plurality of electrodes or any one of said plurality of electrodes and said additional electrode.

10. In an apparatus of the type described, the combination of an electrocardiograph having input terminals, a plurality of at least three electrodes adapted to be in contact with the body of a person during examination, an additional electrode adapted to be placed at will in contact with different points of the body for exploratory purposes, contacts connected to each of said electrodes to constitute an electrical reference point corresponding to each electrode, and switch means for connecting said contacts to establish a fifth electrical reference point and for selectively connecting any combination of pairs of said electrical reference points to said input terminals.

11. In an apparatus of the type described, the combination of an electrocardiograph having input terminals, a plurality of at least three electrodes adapted to be in contact with three limbs of a person during examination, an additional electrode adapted to be placed at will in contact with different points of the body for exploratory purposes, switch means between said input terminals and said electrodes comprising a plurality of contacts each of which is connected with one of said plurality of electrodes, and an additional contact connected to said additional electrode, and movable contact members for alternatively connecting to said input terminals any two of said plurality of contacts or any one of said plurality of contacts and the contact for said additional electrode and to simultaneously connect all of said plurality of contacts with one of said input terminals and the contact for said additional electrode to the other of said input terminals.

12. A system for selectively putting into an electrocardiograph, electrically, voltage values derived from electrodes placed in skin contact with different parts of the body, said system including a group of at least three electrodes adapted to be connected through resistances to provide a neutral point; and an additional exploratory electrode to be placed at will at various points on the body; and a switch having contacts electrically connected, respectively, to the electrodes for establishing said neutral point, said exploratory electrode and said electrodes of said group, at points which exclude said resistances; said switch being interposed between said electrocardiograph and said electrodes and including means for selectively associating the following in electrical pairs: the contact electrically related to said neutral point and said exploratory electrode, the contacts connected directly to any electrode of said group with the contact electrically related to said exploratory electrode, and the contacts electrically connected directly to the electrodes of said group, one with another.

MAJOR SAMUEL WHITE.

REFERENCES CITED

The following references are of record in the file of this patent:

UNITED STATES PATENTS

| Number | Name | Date |
|---|---|---|
| 2,124,208 | Paully | July 19, 1938 |
| 2,193,471 | Both | Mar. 12, 1940 |

*List of references cited in Patent No. 2,400,583*

| | | |
|---|---|---|
| 2,098,695 | Southwick | Nov. 9, 1937 |
| 1,837,913 | Marvin et al. | Dec. 22, 1931 |
| 2,214,299 | Heller | Sept. 10, 1940 |